United States Patent
Kijima (10) Patent No.: US 6,514,375 B2
(45) Date of Patent: Feb. 4, 2003

(54) DRY ETCHING ENDPOINT DETECTION SYSTEM

(75) Inventor: Masato Kijima, Kakogawa (JP)

(73) Assignee: Ricoh Company, Ltd., Tokyo (JP)

( * ) Notice: Subject to any disclaimer, the term of this patent is extended or adjusted under 35 U.S.C. 154(b) by 88 days.

(21) Appl. No.: 09/754,768

(22) Filed: Jan. 4, 2001

(65) Prior Publication Data

US 2001/0010255 A1 Aug. 2, 2001

Related U.S. Application Data

(62) Division of application No. 09/210,925, filed on Dec. 14, 1998, now Pat. No. 6,207,008.

(30) Foreign Application Priority Data

Dec. 15, 1997 (JP) .............................................. 9-345198

(51) Int. Cl.[7] ............................ G01N 21/00; H05H 1/00
(52) U.S. Cl. ................................................. 156/345.25
(58) Field of Search ....................... 156/345.25, 345.24; 216/60; 204/298.32, 192.33; 118/723 R (56) References Cited

U.S. PATENT DOCUMENTS

| | | | |
|---|---|---|---|
| 5,322,590 A | 6/1994 | Koshimizu |
| 5,877,090 A | 3/1999 | Padmapani et al. |
| 5,986,747 A | 11/1999 | Moran |

FOREIGN PATENT DOCUMENTS

| | | |
|---|---|---|
| JP | 5994423 | 5/1984 |
| JP | 1226154 | 9/1989 |

Primary Examiner—Thi Dang
(74) Attorney, Agent, or Firm—Cooper & Dunham LLP (57) ABSTRACT

A method and system for determining a dry etching endpoint, at which a dry etching process should be terminated. The dry etching process is carried out in a plasma etching system and comprises the steps of detecting an intensity of light emission generated in the dry etching process, the light emission being extracted through a window located on a side wall portion of a reaction chamber below a horizontal plane which is defined by a surface of a body to be etch treated. The detected intensity is compared to a predetermined threshold level.

20 Claims, 8 Drawing Sheets

FIG. 5
BACKGROUND SYSTEM

FIG. 7
BACKGROUND SYSTEM

FIG. 8
BACKGROUND SYSTEM

DRY ETCHING ENDPOINT DETECTION SYSTEM

This is a divisional of application Ser. No. 09/210,925 filed Dec. 14, 1998 U.S. Pat. No. 6,207,008.

BACKGROUND OF THE INVENTION

1. Field of the Invention

This invention relates to endpoint detection during dry etching processes such as plasma assisted discharge processing operations. More particularly, the present invention relates to a method and apparatus for such dry etching endpoint detection.

2. Description of the Related Art

A number of etching methods have been utilized in semiconductor device fabrication processes, employing plasma discharges and charged particles produced by such discharges. These etching methods by plasma or dry etch methods have been used more and more widely in device fabrication.

During device fabrication processes, a device portion to be etched typically comprises a layer of a first material disposed on top of a layer of a second different material, with certain portions of the first material exposed to plasma through a mask. The device portion is then subjected to plasma etching. The aim of the plasma etching process is to etch away portions of the first material until the second material is exposed, without etching any of the second material. Therefore, it is critical to determine when the plasma etching process should be terminated.

One of the known methods for monitoring the etching of these layers is to monitor the intensity of the light emission from the plasma discharge. Many processes have particular spectral lines or regions which originate from some chemical constituents in the plasma such as reactant species or plasma etch products. By monitoring the intensity at the wavelength characteristic of these species in the plasma, the concentration of those species in the plasma can be determined, which is directly related to the etching processes.

For example, there is disclosed a method in Japanese Laid-Open Patent Application No. 59-94423, in which (1) the intensity of light emission from certain reaction products is monitored, (2) the second derivatives of the intensity is then calculated with time and (3) an endpoint is determined when the value of the second derivative exceeds a predetermined threshold level.

In this method, however, there have been found several shortcomings such as, for example, fluctuations with time in the light emission intensity which is extracted from a reaction etching chamber, thereby resulting in noises included in the intensity signals. These noises originate from several sources depending, for example, on the method used to generate the plasma and the kind of material to be etched.

When the light emission to be extracted is passing through the material to be etched, emitted light is affected by interference depending on the wavelength of the light thereby resulting in noise occurring in the outputted intensity signals, which will be detailed hereinbelow.

Figure 3:
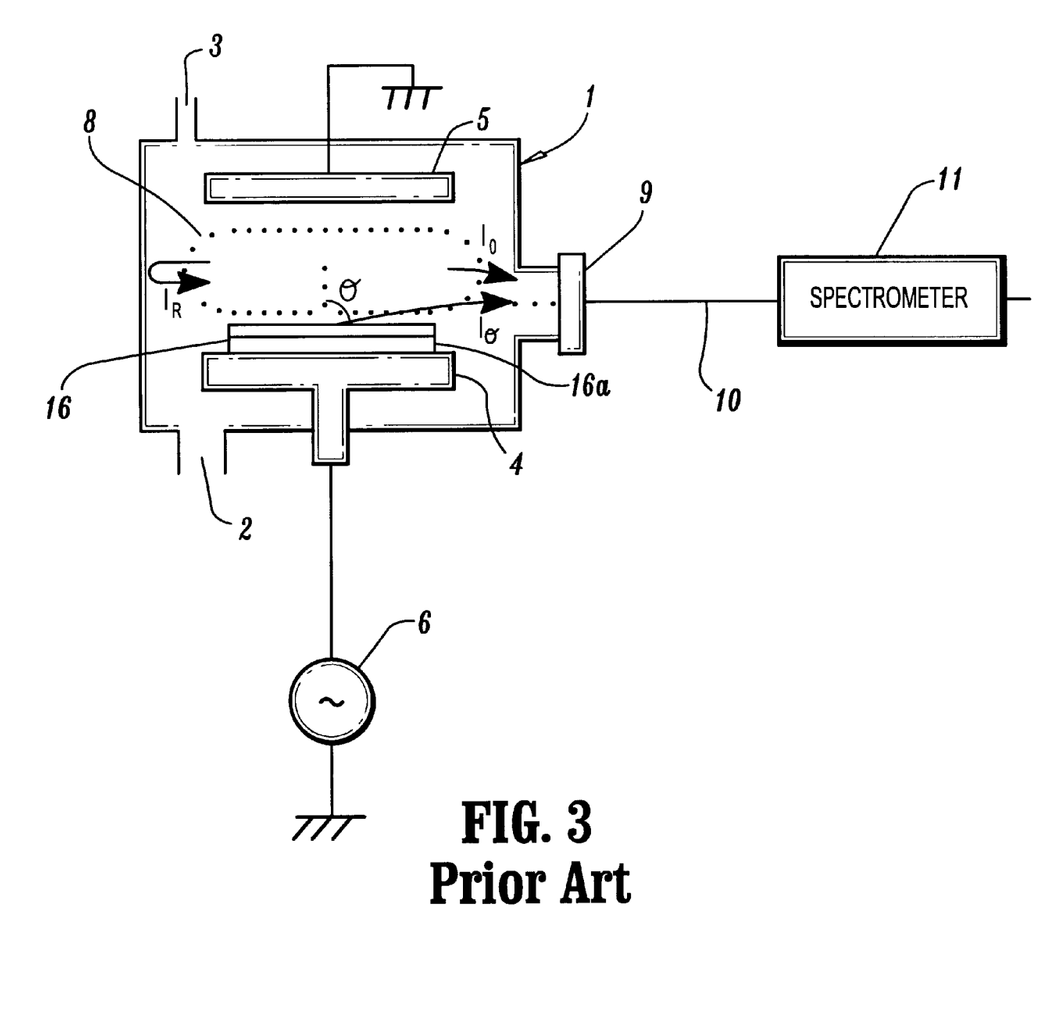
FIG. 3 is a schematic block diagram, illustrating major portions of a background plasma etching system.

FIG. 3 is a schematic block diagram, illustrating major portions of a known plasma etching system. The etching system includes a reaction chamber 1, a body 16 placed therein to be etch treated, a suitable evacuating apparatus (not shown) attached thereto through a connection 2, and a gas feeding system (not shown) also attached thereto through a connection 3 to supply gaseous materials appropriate for the processing. The body 16 is disposed generally on top of a substrate 16a Also provided within the reaction chamber 1 are lower and upper electrodes 4 and 5, having broad faces. These broad faces of the electrodes are placed spaced apart horizontally to form a parallel plate reactor. The lower electrode 4 is supplied with power, generally in the radio-frequency (RF) range, by a power source 6 and serves as a support for the body 16 to be treated. The upper electrode 5 is maintained at ground potential.

Still further, the reaction chamber 1 includes a window 9 provided on a side wall portion thereof, for extracting the light emission which is produced within the chamber 1 by the interaction between the plasma and the body 16 being treated. A fiber optic cable 10 links the window 9 to a spectrometer 11, where the intensity of the extracted light emission at appropriate wavelengths is obtained and transformed further to signal outputs according to the detected intensity.

A shown in FIG. 3, the window 9 has been typically located on the side wall portion of the reaction chamber 1 above the horizontal plane which is defined by the surface of the body 16, and on the same side of the chamber 1 at which plasma processing is taking place. The light emission extracted from the window 9 may therefore include several components such as (1) a component $I_0$ which originates from the plasma region 8 between the electrodes, (2) another component $I_R$ which originates from the reflection by the inner walls of the reaction chamber 1 and (3) still another component $I_\theta$ caused by the reflection from the body 16 being treated, which is assumed to be transparent in the spectral wavelength of the measurements.

Figure 4:
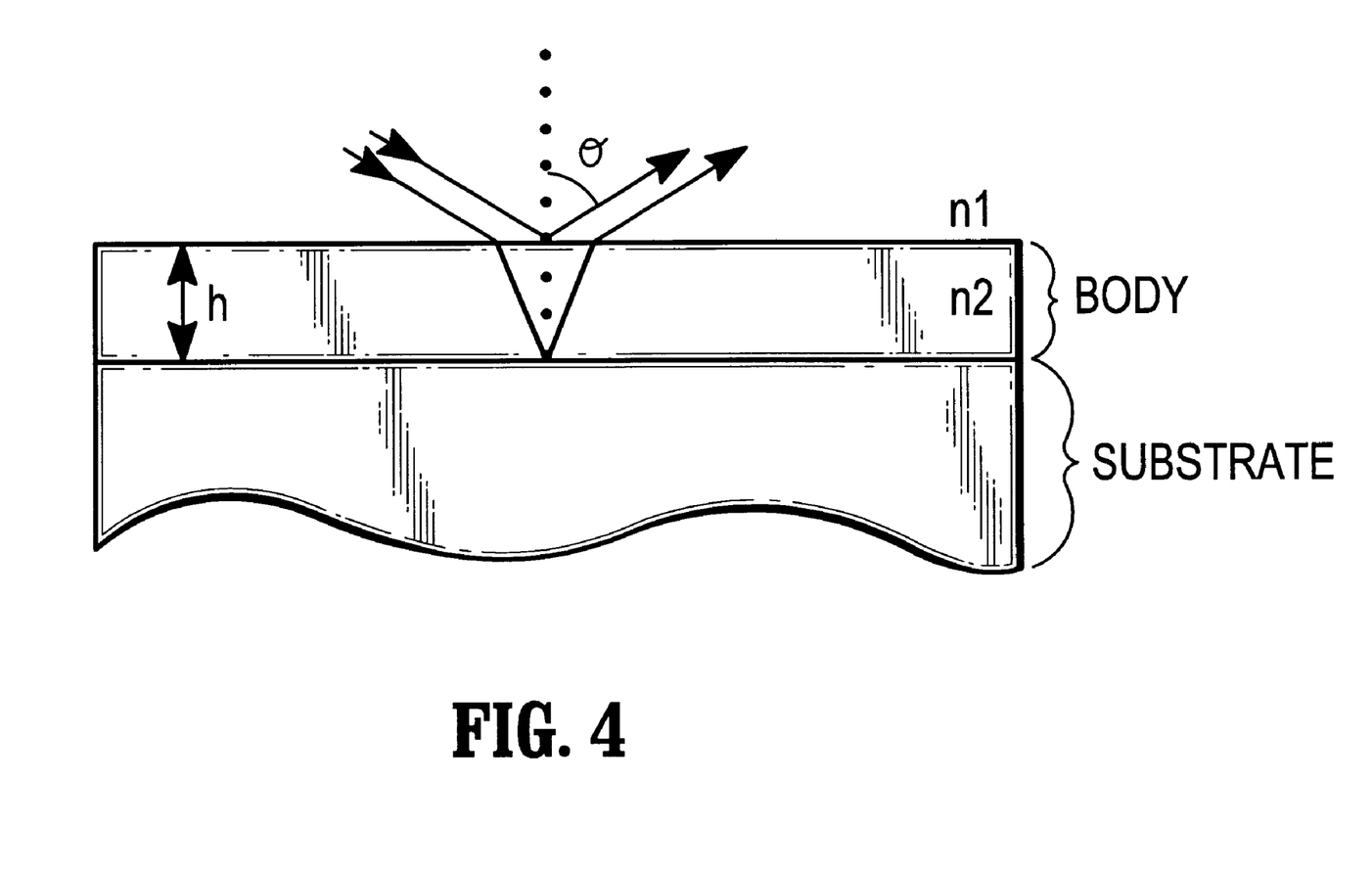
FIG. 4 is a drawing, illustrating the interference of emission light beams in a body being etch treated.

Since the component $I_\theta$ results from the interference of (1) light reflected by the surface of the body 16 and (2) light reflected by the interface between the body 16 and the underlying substrate 16a, as illustrated in FIG. 4, the component $I_\theta$ reflected by the body 16 has an intensity variation with peak intensities under the condition $$2h \cdot \sqrt{(n_2^2 - n_1^2 \cdot \sin^2\theta)} \pm \lambda_0/2 = m \cdot \lambda_0 \qquad (1)$$

$(m=1,2,3,\ldots)$ with h being a thickness of the body 16, $n_1$ a refractive index of the reaction chamber ambience, $n_2$ a refractive index of the body 16, $\theta$ an angle between a reflected light beam and the normal of the surface of the body 16, and $\lambda_0$ a wavelength of light to be detected.

The value h in the above equation (1) decreases as the etching process proceeds, thereby resulting in a periodic change in the emission intensity over time. Accordingly, the amount of change in thickness $h_0$, corresponding to one intensity peak to the next in the $I_\theta$ versus time curve, is expressed by $$h_0 = \lambda_0 / \{2\sqrt{(n_2^2 - n_1^2 \cdot \sin^2\theta)}\} \qquad (2).$$

This results in the period $\tau$ for the aforementioned periodic change as $$\tau = h_0/R \qquad (3)$$

in which R is an etching rate.

As an exemplary illustration, an etching process is assumed in a case where a body 16 composed of a polysilicon layer is etch treated under the following conditions; $n_1$ 1.0, $n_2$ 5.05, $\theta$60° and $\lambda_0$ 426 nanometers. With an etch rate of 300 nanometers/second, $\tau$ is found to be 8.56 seconds.

The aforementioned periodic change in intensity gives rise to concomitant changes in the second derivative values of the light emission intensity which is utilized for determining the endpoints in the aforementioned example. When these changes exceed a predetermined value, this may result in erroneous endpoint detection.

Several methods have been disclosed to obviate the above-mentioned difficulties, such as, for example, by eliminating the periodic changes or fluctuations. For example, Japanese Laid-Open Patent Application No. 1-2261154 discloses several methods, in which an additional "external" means such as a low-pass filter, phase adjusting unit or input signal controller is additionally incorporated in a signal processing circuitry to smooth the fluctuation with time, to thereby eliminate the above periodic changes.

By "external" is meant that this process attempts to eliminate the change after the extraction of light emission or in the course of the signal processing, instead of eliminating it before the extraction or during the collection of light emission inside the chamber. With these methods, the aforementioned difficulties may be obviated to some extent.

Figure 5:
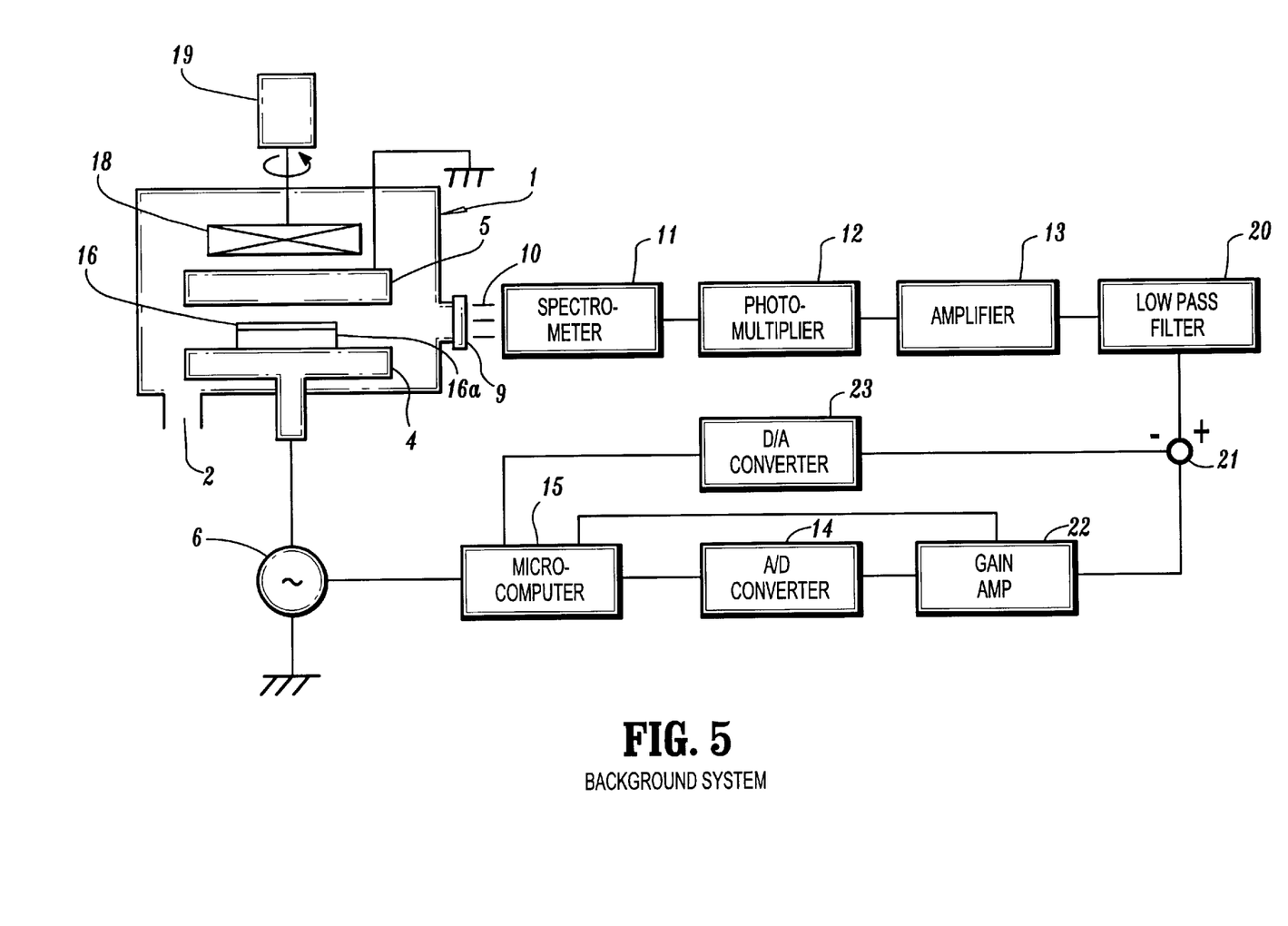
FIG. 5 is a schematic block diagram, illustrating portions of a background plasma etching system further provided with a low pass filter.

Referring to FIG. 5, the above-mentioned method will be exemplified hereinbelow for the case of a plasma etching system with signal processing units incorporating a low-pass filter 20.

The plasma etching system including the reaction chamber is illustrated and described above with respect to FIG. 3. Accordingly, the various portions of FIG. 5 which are common to the system of FIG. 3 are designated with similar numerals and are described only briefly when relevant.

In contrast to the plasma etching system of FIG. 3, the etching system of FIG. 5 is further provided with a dipole magnet 18 which is located spaced apart above the upper electrode 5 and connected to a rotation controlling motor 19 via a rotation axis through the top plate of the reaction chamber 1, so as to rotate the magnet 18 eccentrically around the rotation axis.

A window 9 is provided on a side wall portion of the reaction chamber 1 for extracting the plasma emission which is produced within the chamber 1, originating from chemical constituents in the plasma such as reactant species or plasma etch products. A fiber optic cable 10 links the window 9 to a spectrometer 11 and appropriate wavelengths are selected by a spectrometer 11. The intensity of the extracted light emission at the thus selected wavelengths is transformed to electrical signal outputs by a photomultiplier tube 12, amplified by an amplifier 13, then fed to a low pass filter 20, thereby resulting in amplified intensity signals.

The amplified intensity signals are then fed, through an offsetting adder 21 to a gain amplifier 22, through an analogue-to-digital (A/D) converter 14 and inputted to a microcomputer 15 to be discriminated with respect to a predetermined threshold level.

The microcomputer 15 is configured to be capable of (1) adding offset values to the offsetting adder 21 through the D/A converter 23, (2) adjusting gains of the gain amplifier 22 and (3) turning on or off a power source 6 for the etching system.

An appropriate algorithm is stored in the microcomputer 15, which is capable of detecting an endpoint of the plasma etch processing with respect to a predetermined threshold value. Endpoint detection can be achieved in such a manner, for example, by calculating second derivatives of the emission intensity versus time curve, based on the data outputted from the low pass filter 20, and then comparing the thus obtained value to the predetermined value. Upon detecting an endpoint, the power supplied by power supply 6 for the etching system is terminated by instruction from the microcomputer 15.

Figure 6A:
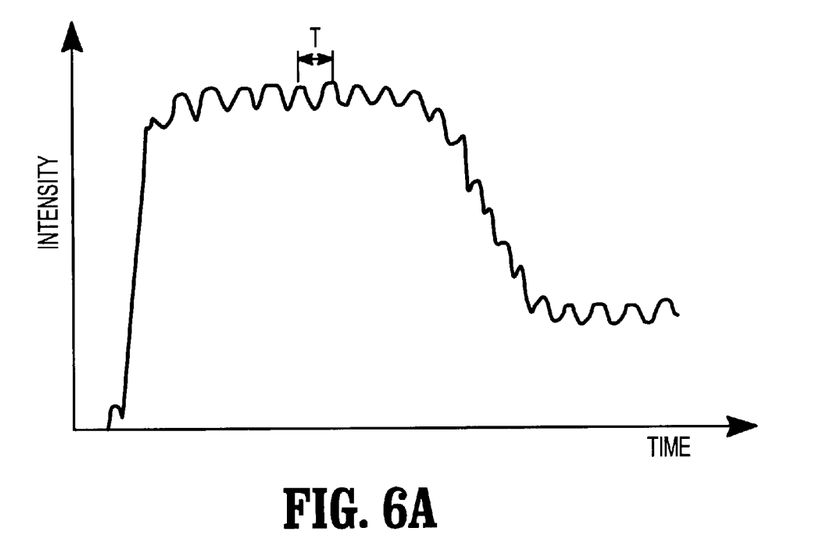
FIG. 6A is a graph, illustrating a change in a signal intensity with time, accompanied by fluctuations with time corresponding to the rotation of a magnet.

With the present construction of the above-mentioned endpoint detection system, the intensity of the light emission changes with the rotation of the dipole magnet 18, and similar changes result in the intensity signals amplified through the photo-multiplier tube 12 and amplifier 13. The change is typically observed as a large gradual change over a relatively long period of time accompanied by smaller changes with a shorter period, caused by the rotation of the magnet 18, as illustrated in FIG. 6A. Namely, the resulting signals generally include noises (or intensity fluctuations with time) with relatively short periods of time.

Figure 6B:
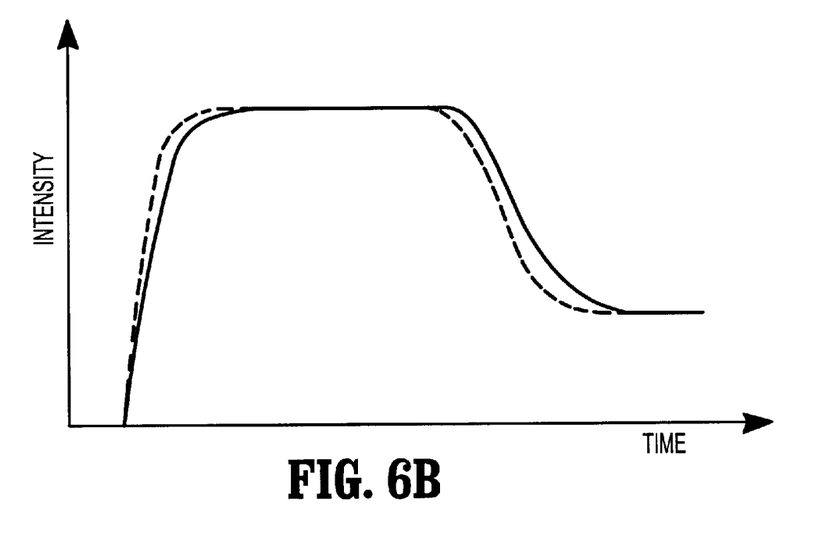
FIG. 6B is a graph, illustrating a change in a signal intensity after being smoothed by a low pass filter.

When the above-mentioned fluctuated signals are fed thorough the low-pass filter 20, the noises with the short period are smoothed to thereby result in a gradual change such as illustrated in FIG. 6B. Therefore, the endpoint detection becomes feasible with more ease with this method.

When feeding the outputted signals through the low pass filter 20 as above, a time delay generally results in the signals being inputted to the microcomputer 15. This is illustrated in FIG. 6B, in which the change of the emission intensity curve without the time delay is shown as a dotted solid curved line, while the delayed signal change obtained after feeding the signal through the low pass filter 20 is shown as a solid curved line.

Figure 7:
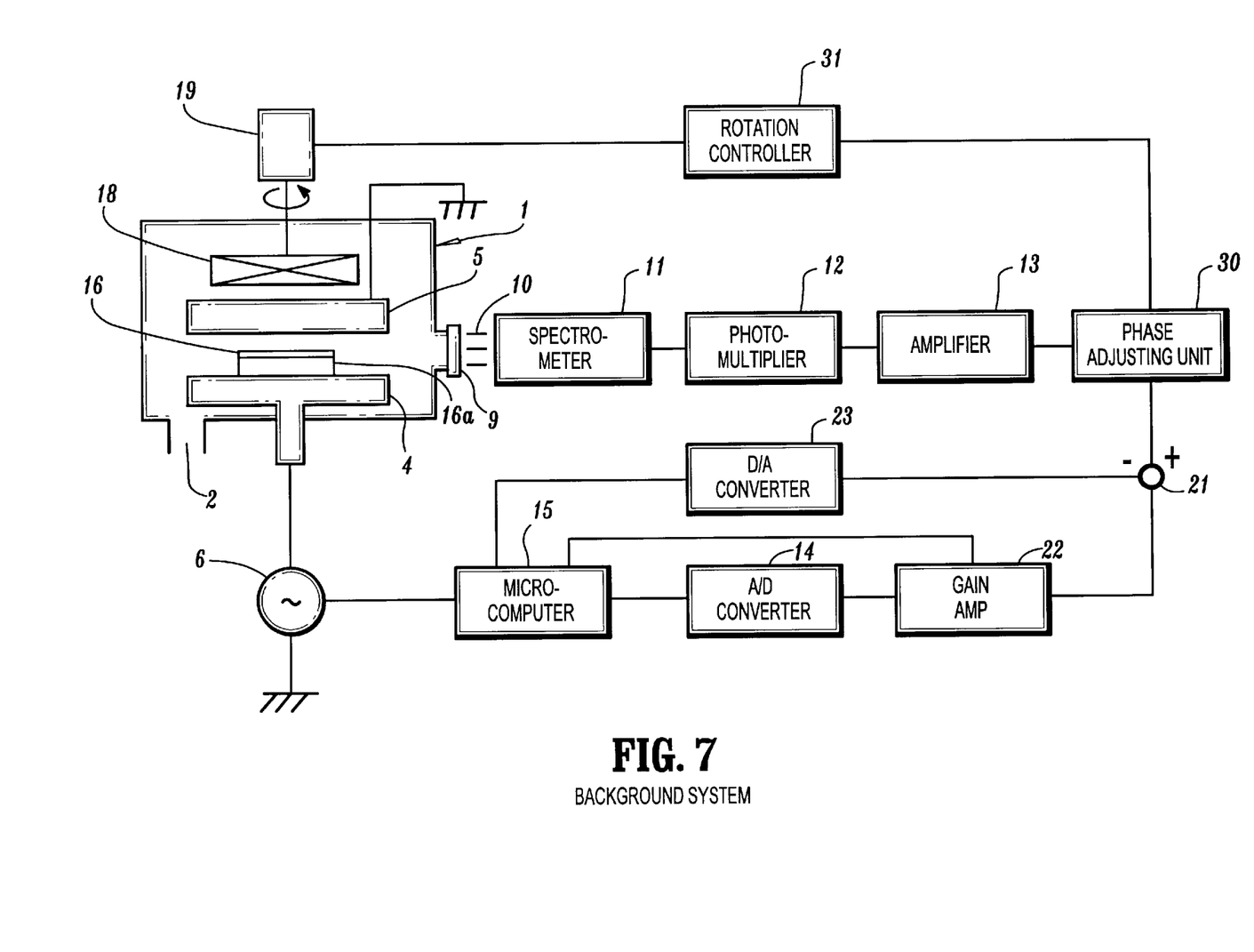
FIG. 7 is a schematic block diagram, illustrating portions of the background plasma etching system of FIG. 5, provided with a phase adjusting unit in place of the low pass filter of FIG. 6B.

In Japanese Laid-open Patent Application '154, there is disclosed another method which additionally incorporates a phase adjusting unit in the signal processing circuitry, as illustrated in FIG. 7.

Referring to FIG. 7, the above-mentioned method will be exemplified hereinbelow, in which the etching system with the signal processing units was already illustrated in FIGS. 3 and 5. Various portions of FIGS. 3 and 5 as described above, are common to the detection system of FIG. 7. Accordingly, the common elements are designated with similar numerals and described only briefly, when relevant.

In contrast to the endpoint detection system of FIG. 5, the plasma processing system of FIG. 7 is provided with a phase adjusting unit 30, in place of the low pass filter 20 of FIG. 5.

When intensity signals are fed into the phase adjusting unit 30, having such fluctuations as shown in FIG. 6A, the intensity signals are processed in the phase adjusting unit 30, such that (1) intensity signals are formed so as to have a certain time delay, or phase shifted, with respect to inputted (or non-phase-shifted) signals and (2) the phase shifted signals are added to the non-phase-shifted signals, to thereby form averaged signals to be outputted. For example, this signal averaging is carried out by (1) forming two sets of signals, each set being phase-shifted by $2\pi/3$ and $2\times 2\pi/3$, respectively, and (2) adding the two sets of signals together with the original non-phase-shifted signals, thereby forming resultant signals.

The timing of the signal addition in the phase adjusting unit 30 is performed synchronously with timing signals from a rotation controller 31, which controls the rotation of the motor 19.

With the present construction of the signal processing units, the above-mentioned fluctuated outputted signals can be smoothed by feeding them into the phase adjusting unit 30, thereby averaging the plurality of sets of intensity signals. The endpoint detection therefore becomes feasible with more ease with this method.

However, feeding the outputted signals through the phase adjusting unit 30, generally results in a certain time delay to the averaged signals caused by the phase shifting process.

Figure 8:
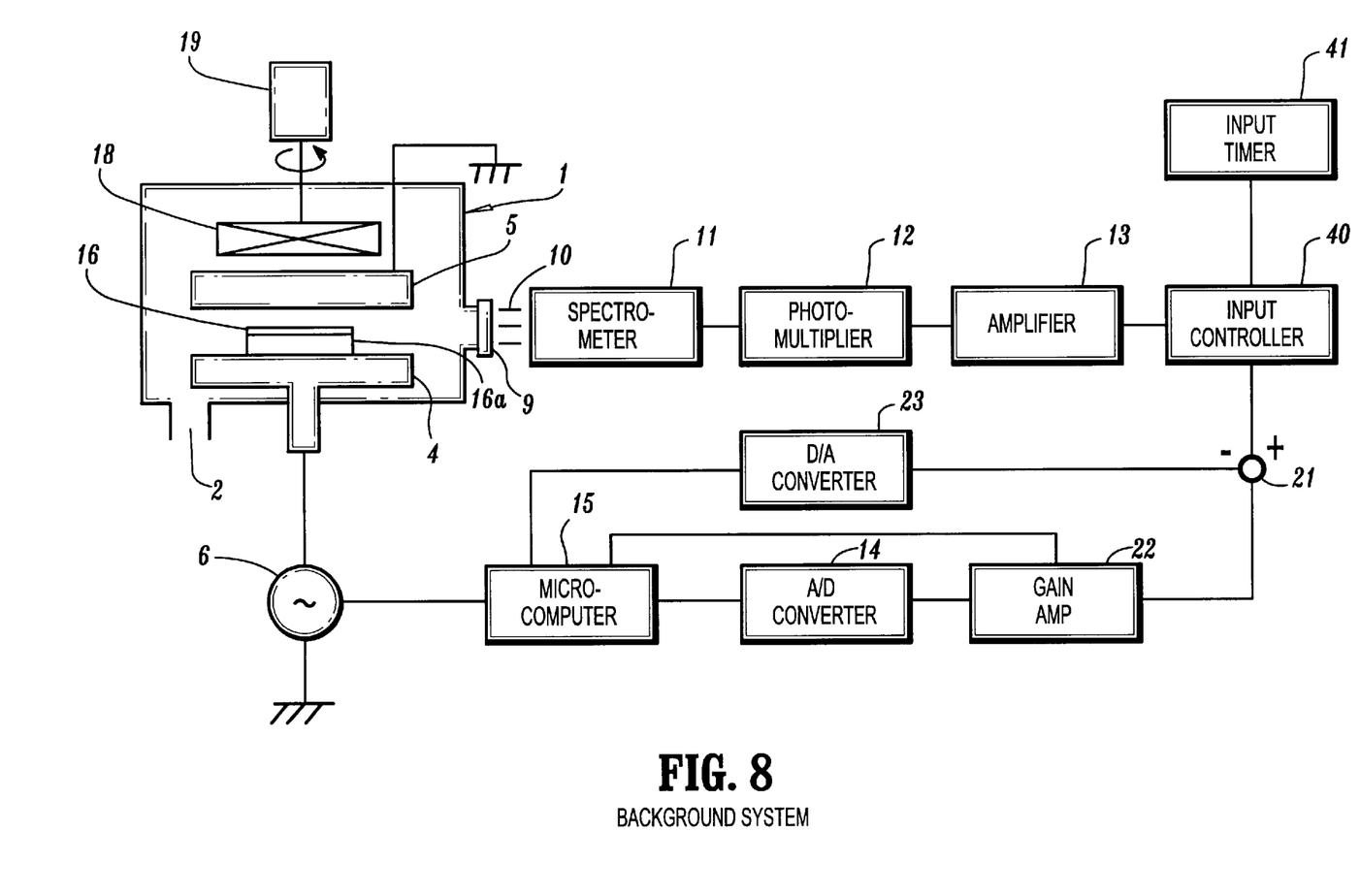
FIG. 8 is a schematic block diagram, illustrating portions of the background plasma etching system of FIG. 5, provided with an input signal controller in place of the low pass filter of FIG. 6B.

In Japanese Laid-open Patent Application '154, there is disclosed still another method which incorporates an input signal controller 40 in the signal processing circuitry, as illustrated in FIG. 8.

Referring to FIG. 8, the above-mentioned method will be exemplified hereinbelow, in which the plasma etching system with signal processing units was already illustrated in FIGS. 3 and 5. Various portions of FIGS. 3 and 5 are common to the system of FIG. 8 and are designated with similar numerals and described only briefly, when relevant.

In contrast to the plasma etching system of FIG. 5, the system of the FIG. 8 is provided with an input signal controller 40 in place of the low pass filter 20 of FIG. 5.

When intensity signals are fed into the input signal controller 40, having such fluctuations as shown in FIG. 6A, the input signal controller 40 carries out sampling according to the period of the fluctuation.

The timing of the signal sampling in an input signal controller 40 is adjusted synchronously with timing signals from input timer 41, which also controls the rotation of the motor 19.

With this construction of signal processing units, the thus obtained signals are considered approximately the same as those intermittently inputted from non-fluctuated signals, and the above-mentioned fluctuated outputted signals from the amplifier 13, can be smoothed by feeding them into the input signal controller 40.

Because of the sampling operation, however, outputted signals are obtained only at a time interval which is equal to the period of the rotation of the motor 19. Therefore, the accuracy of the endpoint detection is affected by the time interval which is inherently included in the sampling method itself.

In these three methods disclosed in Japanese Laid-open Patent Application '154, a motor 19 is used and signal fluctuations result from the rotation of the motor 19. The period of the fluctuation is therefore equal to that of the motor rotation. In addition, since the aforementioned effect of the light interference within, or on the body to be etched, is also dependent upon the rotation, the resultant fluctuation of the collected light intensity therefore has the same period as that of the motor rotation. Therefore, these three methods are also useful to eliminate the interference of emitted light beams.

As described hereinabove, the prior methods of dry etch endpoint detection are useful to a certain extent for their capability of eliminating the noises (or intensity fluctuations with time) of the emission intensity. However, these methods are not completely satisfactory because of a certain time delay induced in the averaged signals caused by the phase shifting process, or the reduced accuracy affected by the time interval associated with the sampling method.

It would therefore be desirable to provide a method and an apparatus for eliminating these errors in the dry etching endpoint detection.

SUMMARY

Accordingly, it is an object of this patent application to provide an improved method and apparatus for eliminating errors in the dry etching endpoint detection, having most, if not all, of the advantages and features of similar employed methods and apparatuses, while eliminating many of the aforementioned disadvantages.

According to an embodiment of the present invention, a method is provided for determining a dry etching endpoint, at which a dry etching process should be terminated, the dry etching process being carried out in a plasma etching system, and comprising the steps of detecting an intensity of light emission generated in the dry etching process, the light emission being extracted through a window located on a side wall portion of a reaction chamber below a horizontal plane which is defined by a surface of a body to be etch treated, and comparing the detected intensity to a predetermined threshold level.

According to an embodiment, the light emission is extracted through the window which is located in the reaction chamber on a side opposite to that of the plasma. The method can further include a step of controlling a temperature of the window. The temperature of the window can be raised and maintained at a predetermined value.

According to another embodiment of the present invention, a dry etching system for carrying out a plasma etching process for a body to be treated, and configured to determine a dry etching endpoint at which a dry etching process should be terminated, comprises a reaction chamber for maintaining a body to be etch treated, the reaction chamber including a window located on a side wall portion of the reaction chamber below a horizontal plane which is defined by a surface of the body to be etch treated. Detection circuitry detects an intensity of light emission generated in the dry etching process and emitted through the window. A comparator compares the intensity of light emission detected by the detection circuitry to a predetermined threshold level. The window can be provided on the reaction chamber on a side opposite to a side including the plasma. The system can further include a heater and a heater controlling unit for heating and controlling a temperature of the window.

Another aspect of the present invention relates to a dry etch reaction chamber comprising a reaction chamber for holding a body to be etch treated and a window provided on a side wall portion of the reaction chamber below a horizontal plane defined by the surface of the body to be etch treated.

BRIEF DESCRIPTION OF THE DRAWINGS

Preferred embodiments are described hereinbelow with reference to the drawings wherein.

DESCRIPTION OF THE ILLUSTRATIVE EMBODIMENTS

Figure 1:
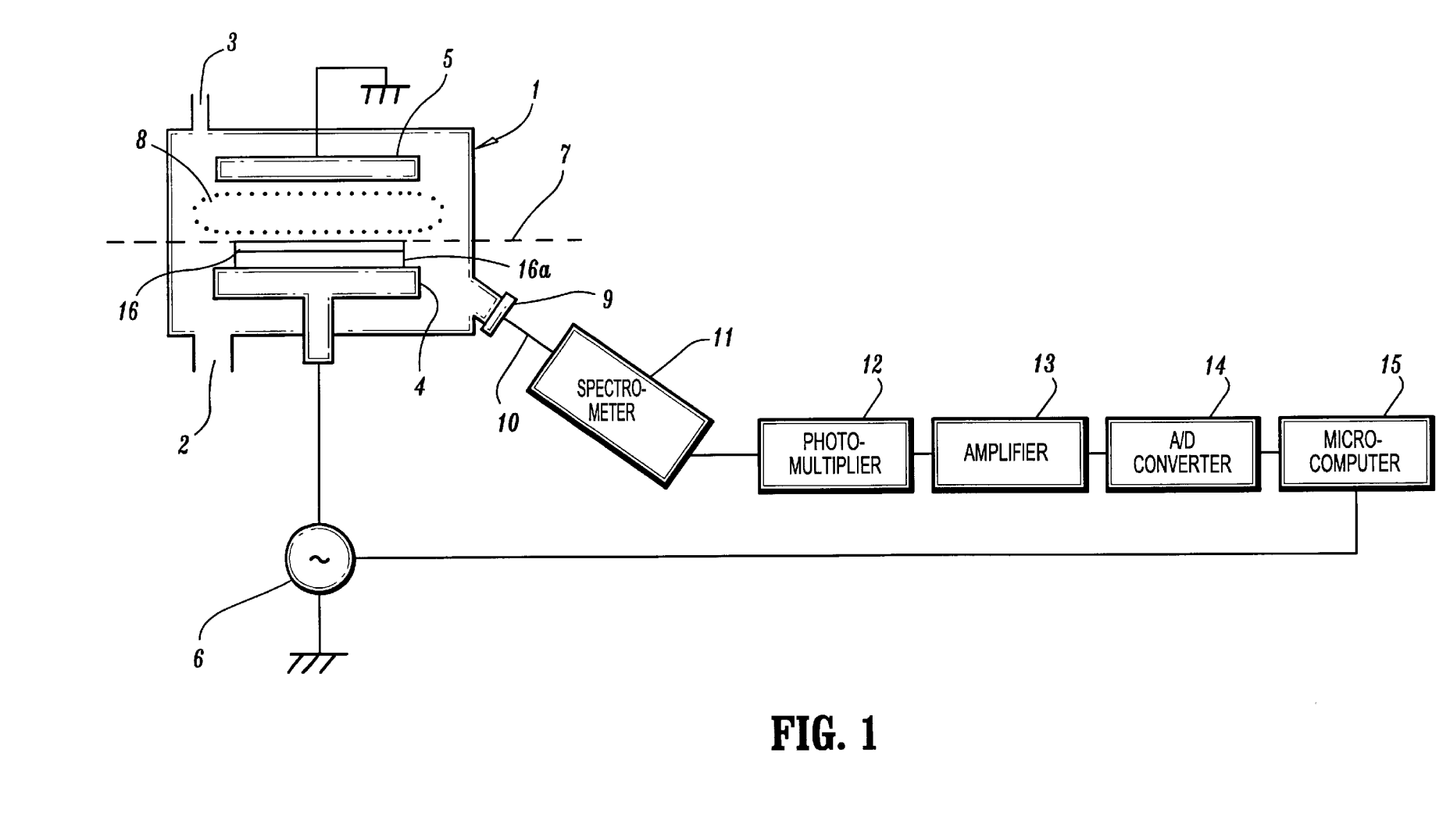
FIG. 1 is a schematic block diagram, illustrating a plasma etching system according to one embodiment disclosed herein.

FIG. 1 is a schematic block diagram, illustrating major portions of a plasma etching system according to one embodiment disclosed herein.

Referring to FIG. 1, the etching system includes a reaction chamber 1, a body 16 (disposed on a substrate 16a)to be treated located therein, a suitable evacuating apparatus (not shown) attached thereto through a connection 2, and a gas feeding unit (not shown) also attached thereto through a connection 3 to supply gaseous materials for etch processing.

Also provided in the reaction chamber 1 are top and bottom electrodes 5 and 4, having broad faces. These broad faces of the electrodes are placed horizontally spaced apart to form a parallel plate reactor. The bottom electrode 4 is supplied with power, generally in the radio-frequency (RF) range, by a power source 6 and serves as a support for the body 16 (and the underlaying substrate 16a) to be treated. The top electrode 5 is maintained at ground potential.

Still further, the reaction chamber 1 includes a window 9 provided on a side wall portion thereof for extracting light emission which is produced within the reaction chamber 1 by the interaction between the plasma and the body 16 being treated.

As aforementioned, the window shown in the background methods for extracting the light emission, has been located above the horizontal plane which is defined by the surface of the body 16, and is on the same side of the reaction chamber 1 as the plasma, in which plasma etching is taking place as illustrated in FIG. 3, for example. However, the Applicant of the present invention has noted that the fluctuations with time in the light emission intensity which is extracted from a reaction etching chamber, which thereby result in noises included in the intensity signals as described above, are also effected from the position of a window thorough which the light emission is extracted. This is in addition to the effects noted above which effect the noises such as the method used to generate the plasma and the kind of material to be etched.

Accordingly, in the present embodiment by contrast, the window 9 is located below the horizontal plane 7 which is defined by the surface of the body 16, and which is on the opposite side of the reaction chamber 1 to the plasma space 8 in which plasma processing is taking place.

In order to detect a dry etching endpoint, a plurality of units are further provided including a spectrometer 11, photomultiplier tube 12, amplifier 13, A/D converter 14 and microcomputer 15.

Light emission is extracted from the space surrounding the body 16 through a window 9 of the reaction chamber 1, and is then lead to the spectrometer 11 through a fiber optic cable 10. The light emission is produced within the chamber 1, and appropriate components of the light emission at predetermined wavelengths are selected by the spectrometer 11 such that these wavelengths are characteristic to chemical constituents in the plasma space 8 such as reactant species or plasma etch products produced during the etching processes.

The intensity of the extracted light emission at the selected wavelengths is then converted to electrical signals by the photomultiplier tube 12. The electrical signals are subsequently amplified by the amplifier 13, transformed into digital signals by the A/D converter 14 and fed to the microcomputer 15.

An algorithm is stored in the microcomputer 15, which is capable of executing an appropriate program which cain determine an endpoint of the dry etching processes with respect to a predetermined threshold level.

By executing the program, an endpoint detection can be accomplished in such a manner, for example, by calculating second derivatives of the light emission intensity versus time curve based on the digital intensity data described above, and comparing the obtained value to the predetermined threshold level. Upon detecting an endpoint, the power supplied by power source 6 for the etching system is terminated by an instruction from the microcomputer 15.

As described earlier, the window 9 is located on a side wall portion of the reaction chamber 1 below the horizontal plane 7 which is defined by the surface of the body 16, and which is on the opposite side of the plasma space 8 in the reaction chamber 1, in which the plasma processing is taking place. Therefore, light beams reflected from the body 16 being processed are not included among the light beams extracted through the window 9.

As aforementioned, although difficulties in the endpoint detection were previously encountered in the background art, because of a certain time delay introduced in the averaging intensity signals or from reduced accuracy originating from an error inherently associated with data sampling, these difficulties can be obviated in the present construction. Therefore, it is not necessary for the dry etching system to be provided with additional circuits or units for smoothing the intensity signals, such as the aforementioned low pass filter 20, phase synthesizing unit 30 or input signal controller 40.

As a result, endpoint detection may be accomplished by eliminating the effects from the interfered light beams from the body 16 being etch treated, without either the effect of the periodic fluctuations of light intensity caused by the reflection or corresponding fluctuations included in the intensity signals amplified through the amplification.

Figure 2:
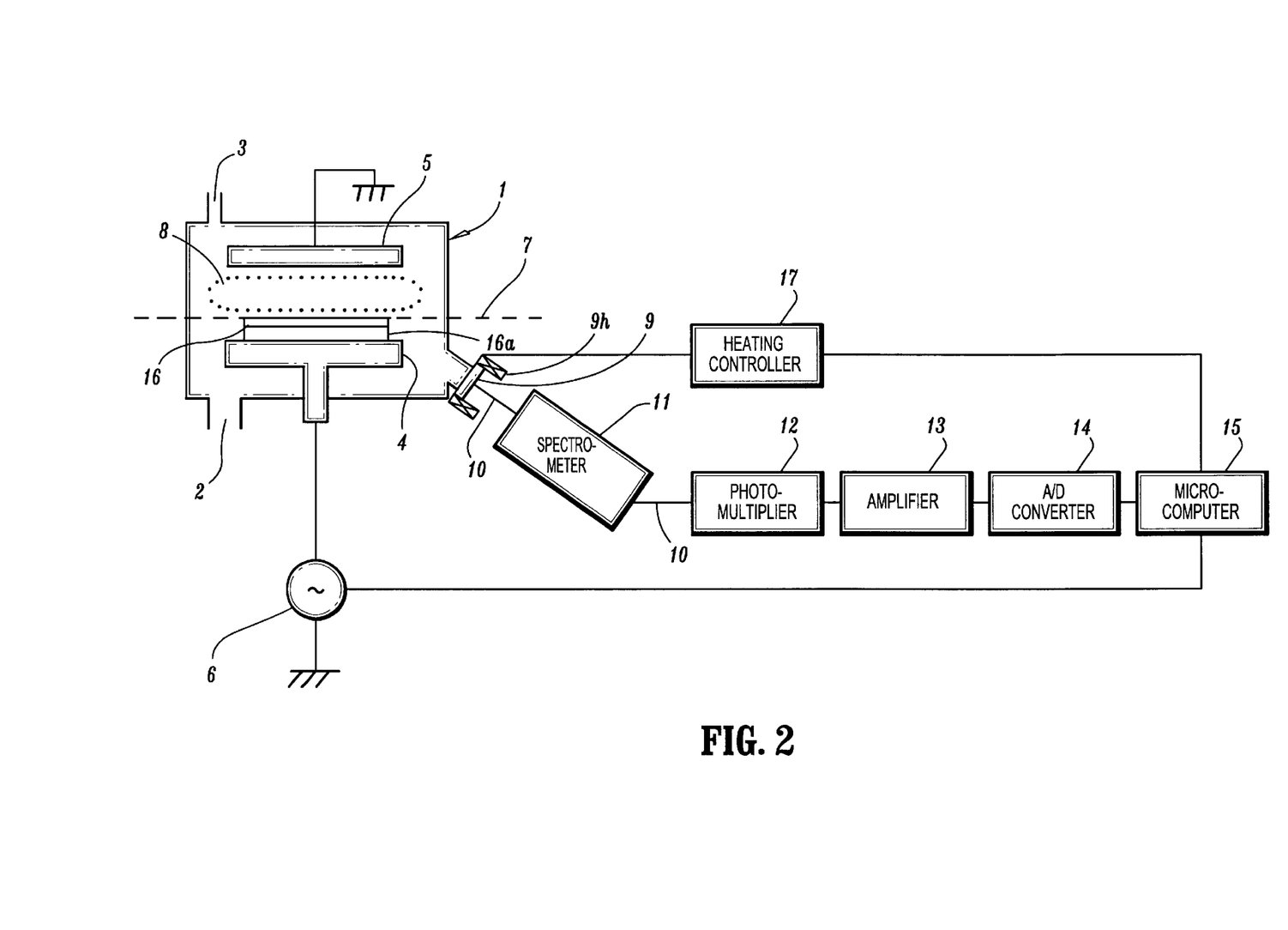
FIG. 2 is a schematic block diagram, illustrating a plasma etching system further provided with a heater and a heater controlling unit, according to another embodiment disclosed herein.

According to the next embodiment, the plasma etching system is further provided with a window heater and a heater controller.

Referring to FIG. 2, the plasma etching system will be described hereinbelow. Since various portions of the etching system shown in FIG. 2 were already illustrated in FIG. 1, the various portions in FIG. 2 which are common to the system of FIG. 1 are designated with similar numerals and described only briefly, when relevant.

The plasma etching system shown in FIG. 2 is provided with a heater 9h for heating the window 9 and a heater controlling unit 17 for controlling a temperature of the window 9 (FIG. 2).

As described earlier, the window 9 is located below the horizontal plane 7 of the body 16 and on the opposite side of the plasma space 8 in the reaction chamber 1. Since the window 9 is therefore exposed less to the plasma atmosphere, the deposition of the by-products of the etching tends to increase on an inner surface of the window 9 during the etch processing, because of the reduced exposure to the plasma and thereby reduced sputtering of the etching products, when compared to that previously deposited on the inner surface by the background methods described above.

In the present embodiment, therefore, it is intended to raise the temperature of the window 9 by heating, thereby preventing the deposition of the etching products. With the heater 9*h* and the heater controlling unit 17, a window temperature is raised and maintained high enough to prevent such deposition.

With the addition of the heater 9*h* and the heater controlling unit 17, the deposition of the etching products on the window 9 can thus-be prevented. As a result, prior difficulties can also be obviated, such as decreases in emission intensities which can occur over time, which is encountered during prolonged etching time or after a number of bodies have been treated (such as, for example, silicon wafers). The present invention is thereby able to maintain stable capabilities for accurately determining etching endpoints.

In addition, since the window 9 is located below the horizontal plane 7 of the body 16 and in the opposite side of the plasma space 8 in the reaction chamber 1 and is exposed less to the plasma atmosphere, as described just above, the raised window temperature will not adversely affect process parameters during the etching processes.

As described hereinabove, the present method of endpoint detection may be applied to the body 16 which can be, for example, a layer of silicon oxide formed on a silicon wafer, or a layer of silicon oxide and another layer of polysilicon formed further thereon on a silicon wafer. The bodies to be etch processed in these examples, are layers of silicon oxide and of polysilicon, respectively.

However, the kinds of bodies to be etched are not limited to these examples. The present method can also be applied with satisfactory accuracy results for endpoint detection, to other materials as well, which may inherently be affected by the aforementioned interference effects.

Although the structure of the plasma etching system has been described specifically with respect to one with parallel plates, it is to be understood that the present endpoint detection method may be applied also to other structures of dry etching systems such as, of magnetron RIE (reactive ion etching), electron cyclotron resonance (ECR) or inductively coupled plasma (ICP).

Still further, although second derivative values have been specifically described hereinabove for the determination of the endpoints in the embodiments of this specification, other intensity parameters may also be used, such as emission intensity versus time curve, or its first derivative with respect to time, each of which is compared to respective predetermined threshold levels.

Additional modifications and variations of the embodiments disclosed herein are possible in light of the above teachings. It is therefore to be understood that within the scope of the appended claims, these embodiments may be practiced otherwise than as specifically described herein.

This document claims priority and contains subject matter related to Japanese Patent Application 9-345198, filed with the Japanese Patent Office on Dec. 15, 1997, the entire contents of which are hereby incorporated by reference.

What is claimed is:

1. A dry etching system for carrying out a plasma etching process for a body to be treated, and configured to determine a dry etching endpoint at which a dry etching process should be terminated, comprising
    a reaction chamber for maintaining a body to be etch treated, the reaction chamber including a window located on a side wall portion of the reaction chamber below a horizontal plane which is defined by a surface of the body to be etch treated;
    detection circuitry for detecting an intensity of light emission generated in the dry etching process and emitted through said window; and
    a comparator for comparing the intensity of light emission detected by said detection circuitry to a predetermined threshold level.

2. A system as recited in claim 1, wherein the window is provided on the reaction chamber on a side opposite to a side including the plasma.

3. A system as recited in claim 1, further comprising a heater and a heater controlling unit for heating and controlling a temperature of said window.

4. A system as recited in claim 3, wherein a temperature of said window is raised and maintained at a predetermined value by controlling said heater with said heater controlling unit.

5. A dry etching system for carrying out a plasma etching processor a body to be treated, and configured to determine a dry etching endpoint at which a dry etching process should be terminated, comprising:
    a reaction chamber for maintaining a body to be etch treated, the reaction chamber including a window located on a side wall portion of the reaction chamber below a horizontal plane which is defined by a surface of the body to be etch treated;
    detection means for detecting an intensity of light emission generated in the dry etching process and emitted through said window; and
    comparing means for comparing the intensity of light emission detected by said detection means to a predetermined threshold level.

6. A system as recited in claim 5, wherein the window is provided on the reaction chamber means on aside opposite to a side including the plasma.

7. A system as recited in claim 6, further comprising heater means and heater controlling means for heating and controlling a temperature of said window.

8. A system as recited in claim 7, wherein the temperature of said window is raised and maintained at a predetermined value by controlling said heater means with said heater controlling means.

9. A dry etch reaction chamber comprising:
    a reaction chamber for holding a body to be etch treated; and
    a window provided on a side wall portion of the reaction chamber below a horizontal plane defined by a surface of the body to be etch treated, for detecting light emission during etch treating.

10. A dry etch reaction chamber as recited in claim 9, further comprising a heater for heating the window.

11. A dry etch reaction chamber as recited in claim 10, further comprising a heater controller for controlling the a temperature of the heater.

12. A dry etch reaction chamber as recited in claim 11, wherein the heater controller is capable of raising a temperature of the heater and window and maintaining the window at a predetermined temperature.

13. A dry etch reaction chamber as recited in claim 9, further comprising first and second connections for evacuating gaseous materials from and supplying gaseous materials to said chamber.

14. A dry etch reaction chamber as recited in claim 9, further comprising top and bottom electrodes placed horizontally spaced apart in the chamber to form a parallel plate reactor.

15. A dry etch reaction chamber as recited in claim 14, wherein the bottom electrode serves as a support for the body to be etch treated.

16. A dry etch reaction chamber as recited in claim 14, wherein the top electrode is connected to ground and the bottom electrode is connected to a power source.

17. A dry etch reaction chamber as recited in claim 16, wherein the power source is an RF power source.

18. A dry etch reaction chamber as recited in claim 9, wherein the window is provided on a side wall of the chamber opposite to a plasma space.

19. A dry etching system for carrying out a plasma etching process for a body to be treated, and configured to determine a dry etching endpoint at which a dry etching process should be terminated, comprising:

a reaction chamber for maintaining a body to be etch treated, the reaction chamber including a window located on a side wall portion of the reaction chamber below a horizontal plane which is defined by a surface of the body to be etch treated, the window leading a light emission generated during the dry etching process out of the reaction chamber;

detection means for detecting an intensity of light emission generated in the dry etching process and emitted through said window; and     comparing means for comparing the intensity of light emission detected by said detection means to a predetermined threshold level.

20. A dry etch reaction chamber comprising:

a reaction chamber for holding a body to be etch treated; and a window provided on a side wall portion of the reaction chamber below a horizontal plane defined by a surface of the body to be etch treated, the window leading a light emission generated during the etch treating out of the reaction chamber.

* * * * *